(12) United States Patent
Cameron et al.

(10) Patent No.: US 10,216,907 B2
(45) Date of Patent: Feb. 26, 2019

(54) ELECTRONIC CALIBRATED MATTER TRANSFER SYSTEM

(71) Applicant: Lunatech, LLC, Studio City, CA (US)

(72) Inventors: John Cameron, Studio City, CA (US); Dean Becker, Fairhope, AL (US); Gene Fein, Oxnard, CA (US)

(73) Assignee: Lunatech, LLC, Encino, CA (US)

( * ) Notice: Subject to any disclaimer, the term of this patent is extended or adjusted under 35 U.S.C. 154(b) by 85 days.

(21) Appl. No.: 15/338,563

(22) Filed: Oct. 31, 2016

(65) Prior Publication Data

US 2017/0124283 A1 May 4, 2017

Related U.S. Application Data

(60) Provisional application No. 62/249,103, filed on Oct. 30, 2015.

(51) Int. Cl.
| | | |
|---|---|---|
| *G07F 19/00* | (2006.01) | |
| *A61J 7/00* | (2006.01) | |
| *G06F 19/00* | (2018.01) | |

(52) U.S. Cl.
CPC ............ *G06F 19/3462* (2013.01); *A61J 7/00* (2013.01); *G06F 19/00* (2013.01)

(58) Field of Classification Search
CPC .... A61J 7/0053; A61J 7/0076; G06F 19/3462
See application file for complete search history.

(56) References Cited

U.S. PATENT DOCUMENTS

| | | | |
|---|---|---|---|
| 4,660,742 A | * 4/1987 | Ozdemir | B67D 1/12 222/153.09 |
| 6,249,717 B1 | * 6/2001 | Nicholson | A61J 7/0481 222/246 |
| 8,757,147 B2 | 6/2014 | Terry et al. | |
| 8,820,330 B2 | 9/2014 | Bellinger | |
| 8,851,083 B2 | 10/2014 | Oglesby et al. | |
| 8,955,522 B1 | 2/2015 | Bowen et al. | |
| 9,408,416 B2 | 8/2016 | Monsees et al. | |
| 9,498,002 B1 | 11/2016 | Soreide | |
| 9,585,981 B2 | 3/2017 | Wynalda, Jr. | |
| 2006/0071011 A1 | * 4/2006 | Varvarelis | A61J 7/0481 221/9 |
| 2006/0250795 A1 | * 11/2006 | Langone | A61L 9/14 362/253 |
| 2007/0042792 A1 | 2/2007 | Perfetto et al. | |
| 2015/0025493 A1 | * 1/2015 | Eggert | A61M 5/2448 604/500 |
| 2015/0161883 A1 | 6/2015 | Satgunam | |

\* cited by examiner

*Primary Examiner* — Timothy R Waggoner
(74) *Attorney, Agent, or Firm* — Hankin Patent Law, APC; Susan L. McCain; Anooj Patel

(57) ABSTRACT

Disclosed are method, systems, and devices for dispensing a material. An example method can comprise receiving dosage information indicating an amount of material to transfer from a holding device to a dispensing device, receiving an instruction to transfer the specified amount of material into the dispensing device, and transferring the specified amount of material from the holding device to the dispensing device.

17 Claims, 7 Drawing Sheets

ELECTRONIC CALIBRATED MATTER TRANSFER SYSTEM

CROSS REFERENCE TO RELATED PATENT APPLICATION

This application claims priority to U.S. Provisional Application No. 62/249,103 filed Oct. 30, 2015, here incorporated by reference in its entirety.

BACKGROUND

Medications, supplements, and other nutrients play an important role in maintain health. Human error can result in overdose, forgetting to take a substance, usage of expired medications, and a variety of other problems. Additionally, dosage information may change as a patient reacts to a medication. Accordingly, there is a need for better devices for managing medications, supplements, and other nutrients.

SUMMARY

It is to be understood that both the following general description and the following detailed description are exemplary and explanatory only and are not restrictive as claimed. Provided are methods, systems, and devices for dispensing a material. In an aspect, an example system can comprise a holding device configured to dispense an amount of material specified by a user, and a dispensing device configured to securely couple to the holding device and receive material from the holding device.

In an aspect, an example method can comprise receiving dosage information indicating an amount of material to transfer from a holding device to a dispensing device, receiving an instruction to transfer the specified amount of material into the dispensing device, and transferring the specified amount of material from the holding device to the dispensing device.

In an aspect, and example method can comprise evaluating medical data associated with user, determining to update a dosage of a material for the user, and providing an instruction to a remote device to update the dosage. The remote device can comprise a holding device configured to hold the material and a dispensing device configured to receive a portion of the material based on the dosage on the user.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
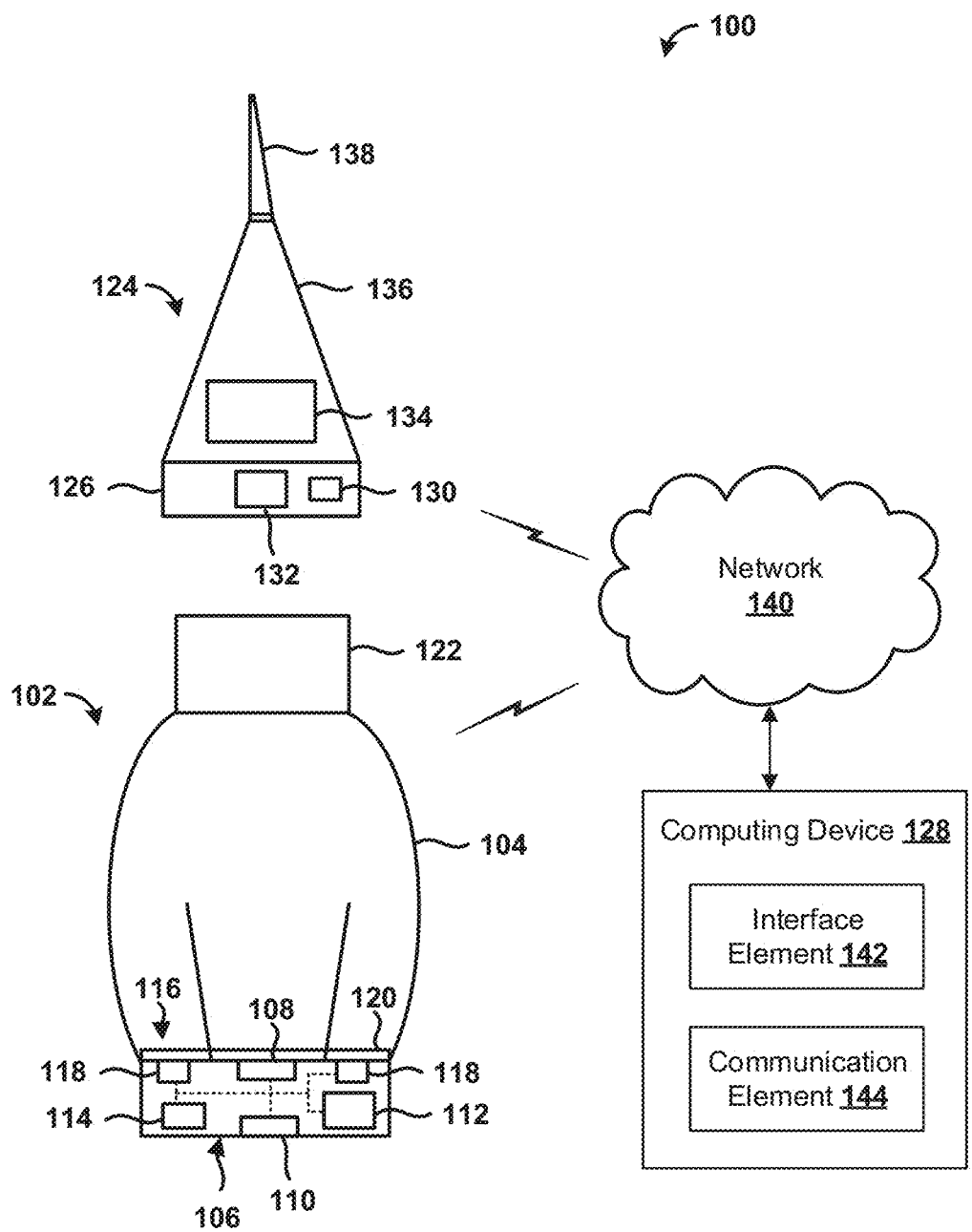
FIG. 1 is a diagram showing a system for dispensing a material.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium.

More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present disclosure relates to creation of a system, method and devices designed to calibrate and distribute exact amounts of a substance between at least two vessels. The process of the transfer of the substance can be locked in place and not subject to tampering or access other than that created by the integrated, sealed system. In another aspect, the present methods and systems can relate to the creation of a bottle and controlled fluid dispenser, called "the needle." The bottle can comprise an electronics package for lighting effects, and a separate control feature for a "human proof" cap.

An electronically tamper proof seal can be accomplished by an airtight locking mechanism. The airtight locking mechanism can be unlocked only once the device has been positioned and verified via matching charge, such as but not limited to 107.8 kh, creating an electronic data 'handshake', software verification, physical hardware lock-and-key matching, etc. This handshake charge/frequency can be reset between devices via password or routine/default security control settings where the exact frequency/charge may be reset as a physical encryption between the devices.

Once unlocked, the dispensing system and needle can then be set to transfer the calibrated and verified dosage based upon the information transferred and verified between the container and needle device, as well as data which may be input via an authorized third party device, such as a physician, or other caregiver, etc.

The holding device and eNeedle (e.g., dispensing device) may be used to hold and deliver medications, wellness ingredients and any material in solid, liquid, or gas form. The calibration takes place as sensors in each of the dispenser and the eNeedle calibrate an amount of material passed from the holding device to the eNeedle via sensor mechanisms, which are verified by multi-point sensing within each device.

Once filled with the calibrated amount of material, material can be dispensed to the user by directly injecting the material into the user or authorized party via the eNeedle, the user or authorized party directly ingesting the material, or transferring the material to a third party receptacle or device such as a hypodermic needle for use. The user can be authorized by fingerprint, voiceprint, password input, retinal scan, microbial 'fingerprint' and the like.

FIG. 1 is a diagram showing a system for dispensing a material. In an aspect, the system 100 can comprise a holding device 102, such as a container, bottle, and/or the like. For example, the holding device 102 can comprise a chamber 104 for storing a material, such as a liquid. The chamber 104 can be transparent, translucent, opaque, and/or the like.

The holding device 102 can be a computerized container. The holding device 102 can comprise a base 106. The base 106 can comprise electrical components. For example, the base 106 can comprise a light 108 configured to illuminate the chamber 104. The light 108 can be actuated via an actuation element 110. For example, the actuation element 110 can be a sensor. The sensor can detect when the container is lifted from a surface (e.g., table, charging plate, etc.). The sensor can comprise a proximity sensor, accelerometer, gyroscope, camera, and/or the like. As another example, the actuation element 110 can comprise a button. Pressing of the button can turn the light on or off.

In an aspect, the actuation element 110 can also be configured to implement security to allow only authorized users to use the holding device 102. For example, the actuation element 110 can comprise authentication input (e.g., sensor, user input element). For example, the authentication input can be a biometric sensor, voice recognition unit, button for inputting a sequence, and/or the like. Once the actuation element has authorized the user (e.g., using the authentication input), then the actuation element can turn on the light and/or other electrical/mechanical components.

In an aspect, the base 106 can comprise a first control unit 112. The first control unit 112 can comprise a processor and memory (e.g., non-volatile, and volatile memory). The first control unit 112 can also comprise a transmitter configured to receive and/or send information remotely. Information can comprise dosage information (e.g., how much of the material to dispense. The information can further comprise usage information and/or a history of how much material was dispensed for corresponding users. The usage information can comprise time stamps indicating when the material was dispensed. In an aspect, the base 106 can comprise a power source 114, such as a battery, solar panel, thermal power source, motion induced power source, and/or the like. The power source 114 can be configured to provide power to the first control unit 112, actuation element 110, light 108, transducer 116, and/or other mechanical and/or electrical elements of the holding device 102.

In an aspect, the base 106 can comprise a transducer 116 configured to apply a pressure to material. For example, the transducer 116 can comprise one or more motors 118 for operating a plate 120. The plate 120 can be at least partially disposed within the chamber. The transducer 116 can be configured (e.g., by the first control unit 112, via calibration) to apply a specified pressure to the material in order to dispense a specified amount of the material. For example, the first control unit 112 can instruct the transducer 116 to dispense a specified amount of the material (e.g., 1 oz, 1 gram, any appropriate number, etc) by sending a signal to the one or more motors 118. It should be understood that pressure can be applied by other mechanisms, such as a device configured to provide air pressure (e.g., fan), a heating element (e.g., heating the material to increase the pressure, and/or the like.

Figure 2:
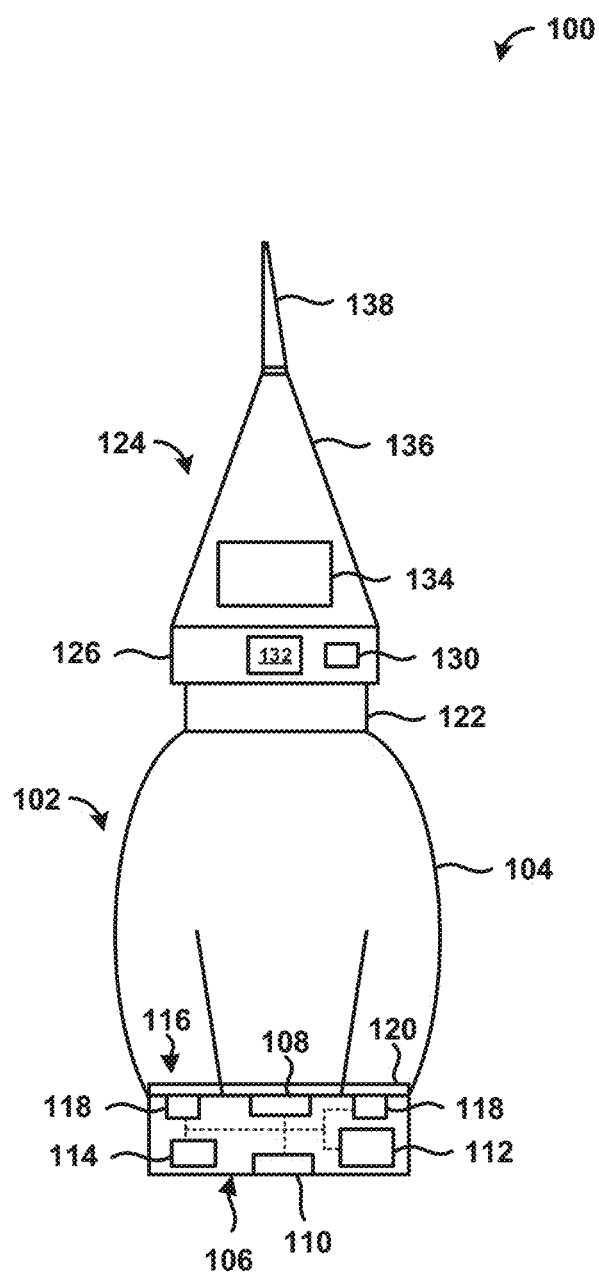
FIG. 2 is another view of the system for dispensing material.

In an aspect, the holding device 102 can comprise a cap 122. The cap 122 can be configured to prevent the material from escaping the chamber 104. The cap 122 can be configured to mechanically and/or electrically couple the holding device 102 to a dispensing device 124. The dispensing device 124 can comprise a dispensing control element 126. The dispensing control element 126 can be configured to mechanically and/or electrically couple with the cap 122. For example, the dispensing control element 126 and the cap 122 can be configured to securely couple to each other, as shown in FIG. 2. For example, the dispensing control element 126 and/or the cap 122 can be configured to generate magnetic fields and/or electric fields using electric charge to attach together. The dispensing control element 126 can be configured to fit over the cap 122. The dispensing control element 126 and/or the cap 122 can be configured to apply a seal by use of a mechanical latch, clamping devices, twist-action latch, and/or the like. The dispensing control element 126 and/or the cap 122 can be configured to form the seal (e.g., attach to each other) based on an authentication technique. For example, the dispensing control element 126 and/or the cap 122 can be configured to transmit authentication information. The authentication information can comprise encrypted data, encryption keys, and/or the like. The authentication information can be provided to the dispensing control element 126 and/or the cap 122 from a remote device, such as a computing device 128. In another aspect, the authentication information can comprise the magnetic field and/or electrical field generated by the dispensing control element 126 and/or the cap 122. For example, the dispensing control element 126 and/or the cap 122 can be configured to seal (e.g., attach) to another device having a specified magnetic field, electrical field, and/or the like.

In an aspect, the dispensing device 124 can comprise one or more same or similar components as the holding device 102. For example, the dispensing device can comprise a second control unit 130. The second control unit 130 can comprise a processor, memory, transmitter, and/or other components. In some implementations, the first control unit 112 or the second control unit 130 can be omitted, such that either the holding device 102 or the dispensing device has a control unit for controlling one or both of the holding device 102 and the dispensing device 124. The dispensing device 124 can comprise additional elements not shown, such as actuation elements, input devices, batteries, and/or the like. For example, the dispensing device 124 can be configured for user authentication in a manner similar to the holding device 102. The dispensing device 124 can also be configured to store usage information and communicate with remote devices similarly as described herein for the holding device 102.

For example, the dispensing device 124 can comprise a pressure component 132. The pressure component can be a transducer similar to the transducer 116 of the holding device 102. The pressure component 132 can be configured to provide pressure, such as negative pressure, to draw (e.g., via suction) the material out of the holding device 102 and into the dispensing device 124. The pressure component 132 can be configured (e.g., by the first control unit 112 and/or second control unit 130, via calibration) to apply a specified pressure to the material in order to dispense a specified amount of the material. The pressure component 132 can comprise, for example, a pump configured for pumping the material out of the holding device 102. For example, the first control unit 112 and/or second control unit 130 can instruct the pressure component 132 to suction, pump, siphon, and/or the like X (e.g., 1 oz, 1 gram, any appropriate number, etc) amount of the material by sending a signal to the pressure component 132 (e.g., or fans, motors, electrical or mechanical elements thereof). The pressure component 132 can be calibrated such that specific signals to the pressure component result in a desired amount of material being removed from the holding device 102.

In an aspect, the dispensing device 124 can comprise a display 134. The display can display dosage information, providing messages from remote device, display reminders. The display 134 can also be an input device configured to allow users to authenticate with the dispensing device 124, specify dosage (e.g., how much material to dispense from the holding device 102, allow configuring of user settings, and/or the like.

In an aspect, the dispensing device 124 can comprise a receptacle 136 for holding the material received from the holding device 102. The receptacle 136 can be coupled to a needle 138 or other dispensing component (e.g., tube, straw, etc.). The receptacle 136 can provide the material to the needle 138 for dispensing to a user or other subject (e.g., patient). The needle 138 can be configured to pierce skin, tissue, muscle, and/or like to allow injection of the material into a user.

An electronics package (e.g., light 108, first control unit 112) on the base 106 of the holding device can light up when the dispenser bottle/container is raised into the air or is no longer seated with the base 106 on a surface. This illumination can assist the user in visually verifying the transfer between the holding device 102 and the dispensing device 124. Once the transfer has been completed between the holding device 102 and dispensing device 124, the light 108 can turn off and/or a beeping or other audio effect noise can be generated, by either or both of the holding device 102 and the dispensing device 124. For example, a light may appear to light green or other color on the dispensing device 124. This can be the only alert a user receives, or there can be a second alert letting the user know that the user can remove the holding device 102 from the dispensing device 124, or else that the holding device 102 and/or the dispensing device 124 have been physically disengaged.

In an aspect, the system 100 can comprise a network 140 communicatively coupling the holding device 102, dispensing device 124, and one or more remote devices, such as the computing device 128. In one aspect, the network 140 can comprise a packet switched network (e.g., internet protocol based network), a label-switched network, and/or the like. The network 140 can comprise network adapters, switches, routers, modems, and the like connected through wireless links (e.g., radio frequency, satellite) and/or physical links (e.g., fiber optic cable, coaxial cable, Ethernet cable, or a combination thereof). The network 140 can comprise public networks, private networks, wide area networks (e.g., Internet), local area networks, and/or the like. In one aspect, the network 140 can be configured to provide communication from telephone, cellular, modem, and/or other electronic devices to and throughout the system 100.

In an aspect, the computing device 128 can comprise a user device, a server, a local device, a remote device, and/or the like. For example, the computing device can comprise a computer, a smart device (e.g., smart phone, smart watch, smart glasses, smart apparel, smart accessory), a laptop, a tablet, a set top box, a display device (e.g., television, monitor), digital streaming device, proxy, gateway, transportation device (e.g., on board computer, navigation system, vehicle media center), and/or the like. In an aspect, the computing device 128 can be configured to transmit and/or receive information to or from the holding device 102 and/or dispensing device 124. For example, the computing device 128 can receiving usage information as described herein. The computing device 128 can transmit dosage information (e.g., dosage amount, frequency of dosage, etc.). For example, the computing device 128 can be managed by a third party, such as a doctor, health care provider, hospital, medical facility, research group, and/or the like. The third party can provide updated dosage information for one or more users based on test results, clinical visits, and/or the like. In an aspect, the computing device 128 can be configured to authorize or de-authorize usage of the dispensing device 124 and/or holding device 102. Upon a triggering event, such as when a prescription expires, medication reaches an expiration date, a product recall is announced, etc., the computing device (e.g., user or third party) can instruct the dispensing device 124 and/or holding device 102 to de-authorize (e.g., no longer allow dispensing of the material to a user or any user) dispensing of the material.

In one aspect, the computing device 128 can comprise an interface element 142 configured to provide an interface to a user to interact with the computing device 128 and/or remote devices. The interface element 142 can be any interface for presenting and/or receiving information to/from the user, such as user feedback. An example interface can comprise a content viewer, such as a web browser (e.g., Internet Explorer®, Mozilla Firefox®, Google Chrome®, Safari®, or the like), media player, application (e.g., web application, mobile application, media device application), and/or the like. Other software, hardware, and/or interfaces can be used to provide communication between the user and one or more of the dispensing device 124, the holding device 102, and/or other local or remote devices.

In an aspect, the interface element 142 can provide an interface for accessing usage information for the dispensing device 124 and/or holding device 102. A record of usage of the devices can be chronicled and archived via transmission to authorized user accounts. The user's account can be accessed by the user and authorized third parties. Users can then verify times and dosages received. For example, if the user has forgotten or simply would like to verify the usage information, then the user can access the computing device 128 to remembering whether or not medication was taken, and taken in the proper dose.

In an aspect, the computing device 128 can comprise a communication element 144. As an example, the communication element 144 can request or query various files from a local source and/or a remote source. As a further example, the communication element 144 can transmit and/or receive data to a local or remote device such as the holding device 102, dispensing device 124, and/or other devices (e.g., third party managed device, server, dosage server). The communication element 144 can comprise hardware and/or software to facilitate communication. For example, the communication element 144 can comprise one or more of a modem, transceiver (e.g., wireless transceiver)), digital-to-analog converter, analog-to-digital converter, encoder, decoder, modulator, demodulator, tuner (e.g., QAM tuner, QPSK tuner), and/or the like.

FIG. 2 through FIG. 5 illustrate additional embodiments of the holding device 102 and dispensing device 124 of FIG. 1. FIG. 2 is another view of the system 100 of FIG. 1 in which the holding device 102 and the dispensing device 124 are sealed, attached, joined, and/or the like for transferring of material from the holding device 102 to the dispensing device 124.

Figure 3:
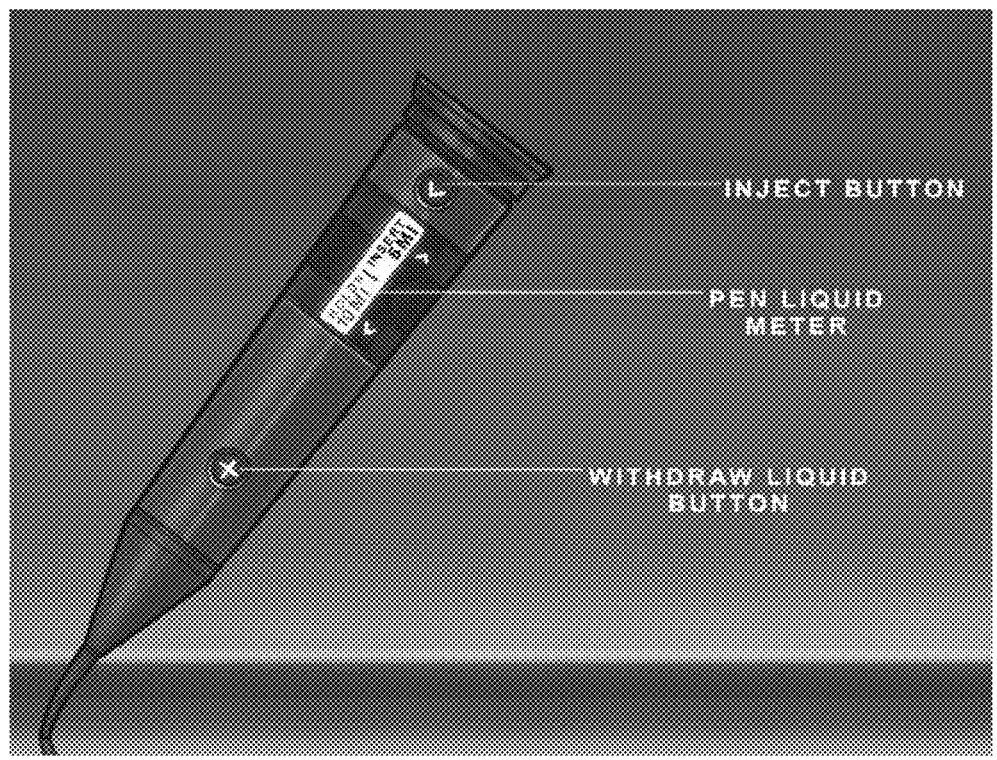
FIG. 3 shows an example dispensing device.

FIG. 3 shows an example dispensing device 124 (e.g., eNeedle). For example, the dispensing device 124 can comprise an inject button configured to inject the material into a user. The dispensing device 124 can comprise a pen liquid meter configured to show information about the material such as total material (e.g., in the holding device 102 or dispensing device 124, dosage information (e.g., how much material to draw from the holding device 102), and/or other information. The dispensing device can comprise a withdraw liquid button configured to cause material to be withdrawn from the holding device 102 (e.g., based on the dosage).

Figure 4:
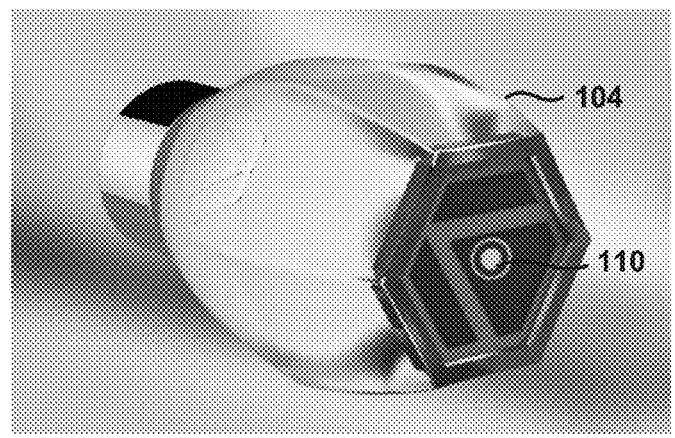
FIG. 4 is a bottom view of an example holding device.
Figure 5:
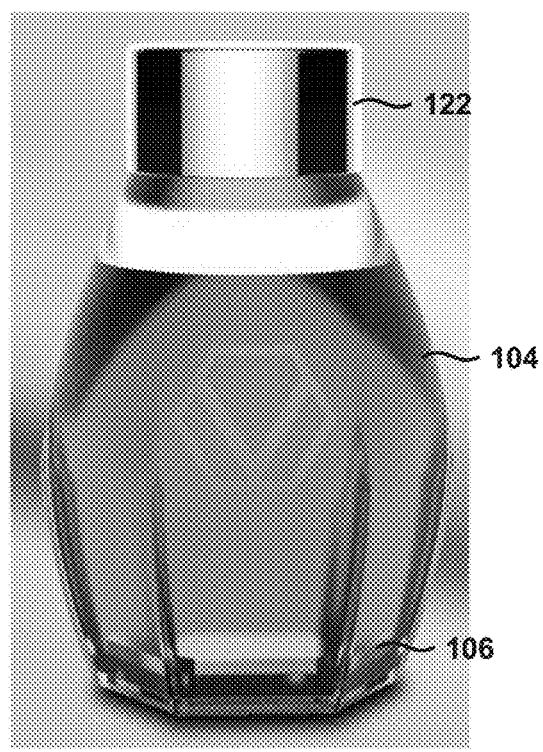
FIG. 5 is a side view of the example holding device.

FIG. 4 is a bottom view of an example holding device 102 (e.g., eBottle), and FIG. 5 is a side view of the example holding device 102. An example chamber 104 is shown with a base 106. As shown, the base 106 can be at least partially or fully within the chamber 104. An example actuation element 110 is also shown for actuation the light, authenticating a user, and/or the like. A cap 122 is shown for preventing material from escaping the chamber 104.

Figure 6:
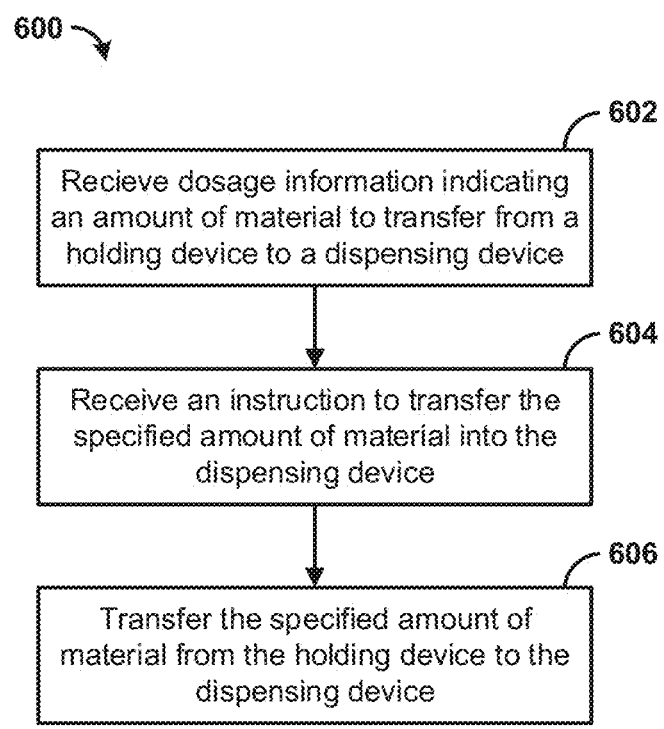
FIG. 6 is a flow chart of an example method for dispensing material.

FIG. 6 is a flow chart of an example method for dispensing material. At step 602, dosage information indicating an amount of material to transfer from a holding device to a dispensing device can be received. At step 604, an instruction to transfer the specified amount of material into the dispensing device can be received. At step 606, the specified amount of material can be transferred from the holding device to the dispensing device. The method 600 can further comprise authenticating a user. The dosage information and the instruction are received from the user. The method 600 can further comprise transmitting dosage information, authorization information, or a combination thereof from one or more of the dispensing device and holding device to a remote device. The remote device can be configured to receive usage history from one or more of the dispensing device and holding device.

The holding device can comprise a security component for authorizing the user, wherein the security component can comprise a biometric sensor, input for entering a security code, or a radio configured to authorized a user when receiving an encrypted signal. The holding device can comprise a memory storing a usage history, wherein the usage history comprises dispensing amounts, dispensing times, and users authorizing the dispensing of the material. The holding device can comprise a chamber for storing the material and a cap for preventing escape of the material. The holding device can comprise a light configured to illuminate the chamber. The holding device can comprise a base having an electronic assembly configured to control the holding device.

The dispensing device can comprise a hollow needle having a pointed end for injecting material. The dispensing device can comprise a pressure component configured to create negative pressure in the dispensing device, thereby causing a specified portion of the material to be transferred to the dispensing device. The dispensing device can comprise an first opening configured to fit over and securing fasten to a second opening of the holding device. The dispensing device can fastens to the holding device by an electromagnetic locking component configured to generate a magnetic field that pulls the dispensing device and holding device together.

Figure 7:
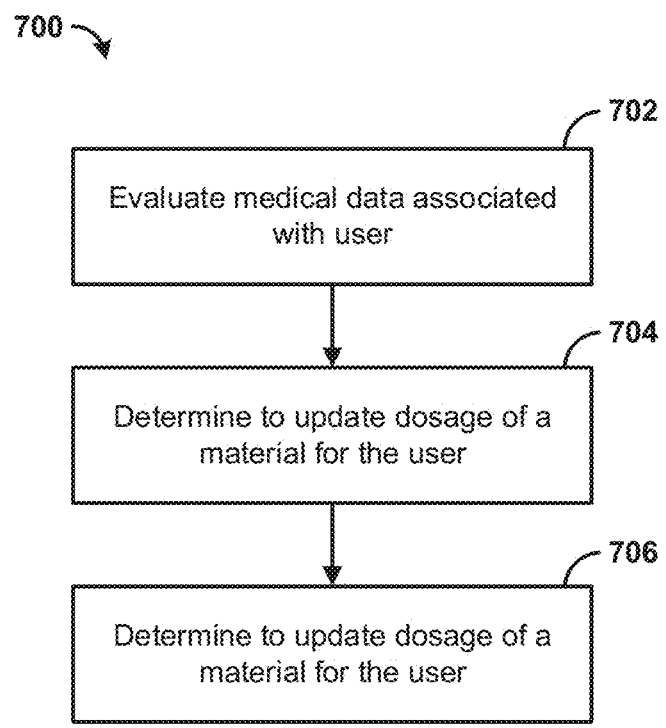
FIG. 7 is a flowchart of an example method for managing a dispensing device.

FIG. 7 is a flowchart of an example method for managing a dispensing device. At step 702, medical data associated with user can be evaluated. For example, changes in the medical data can be determined for a time period. One or more diagnosis, medical history, imaging data, test data, and/or the like can be evaluated and/or trigger a change in dosage (e.g., change dosage amount, starting or ending a medication or nutrient. For example, test data can comprise disease tests, genetic test, cholesterol, blood pressure tests, heart rate information (e.g., rate, ekg), and/or the like.

At step 704, a determination can be made to update dosage of a material for the user. For example, the positive or negative result of test can trigger a change in dosage. The detecting of a test result above or below a result can trigger a change in dosage. The diagnosis of a disease, detection of a virus, bacteria, or other pathogen can trigger a change in dosage. Genetic information and determination of an association with a risk factor can trigger a change in dosage. The lack of payment of a bill can trigger a change in dosage. Real time data associated with the user, such as location, blood alcohol level, blood pressure, blood sugar levels, movement (e.g., rest, sleep, level of consciousness) and/or the like can trigger change in dosage.

At step 706, an instruction can be provided to a remote device to update the dosage. The remote device can comprise a holding device configured to hold the material and a dispensing device configured to receive a portion of the material based on the dosage on the user.

The method 700 can further comprise providing an instruction to transfer the portion of the material from the holding device to the dispensing device based on the update to the dosage. The method 600 can further comprise authenticating a user. The dosage information and the instruction are received from the user. The method 600 can further comprise transmitting dosage information, authorization information, or a combination thereof from one or more of the dispensing device and holding device to a server or user device. The server or user device can be configured to receive usage history from one or more of the dispensing device and holding device.

The holding device can comprise a security component for authorizing the user, wherein the security component can comprise a biometric sensor, input for entering a security code, or a radio configured to authorize a user when receiving an encrypted signal. The holding device can comprise a memory storing a usage history, wherein the usage history comprises dispensing amounts, dispensing times, and users authorizing the dispensing of the material. The holding device can comprise a chamber for storing the material and a cap for preventing escape of the material. The holding device can comprise a light configured to illuminate the chamber. The holding device can comprise a base having an electronic assembly configured to control the holding device.

The dispensing device can comprise a hollow needle having a pointed end for injecting material. The dispensing device can comprise a pressure component configured to create negative pressure in the dispensing device, thereby causing a specified portion of the material to be transferred to the dispensing device. The dispensing device can comprise an first opening configured to fit over and securing fasten to a second opening of the holding device. The dispensing device can fastens to the holding device by an electromagnetic locking component configured to generate a magnetic field that pulls the dispensing device and holding device together.

In an aspect, one or more of the dispensing device and the holding device can be configured to enforce the dosage by preventing dispensing of the material. For example, one or more of the dispensing device and the holding device can be configured to prevent dispensing of the material if the dosage is not yet due to be taken. One or more of the dispensing device and the holding device can be configured to provide an alert indicating that the dosage has already been taken. The alert can be provided via a dummy light, audio sound, or a combination thereof. The dispensing device and the holding device can be configured to provide an alert indicating a time for taking the dosage is due or overdue. The alert can be provided by a beep, vibration, a light, or a combination thereof.

Figure 8:
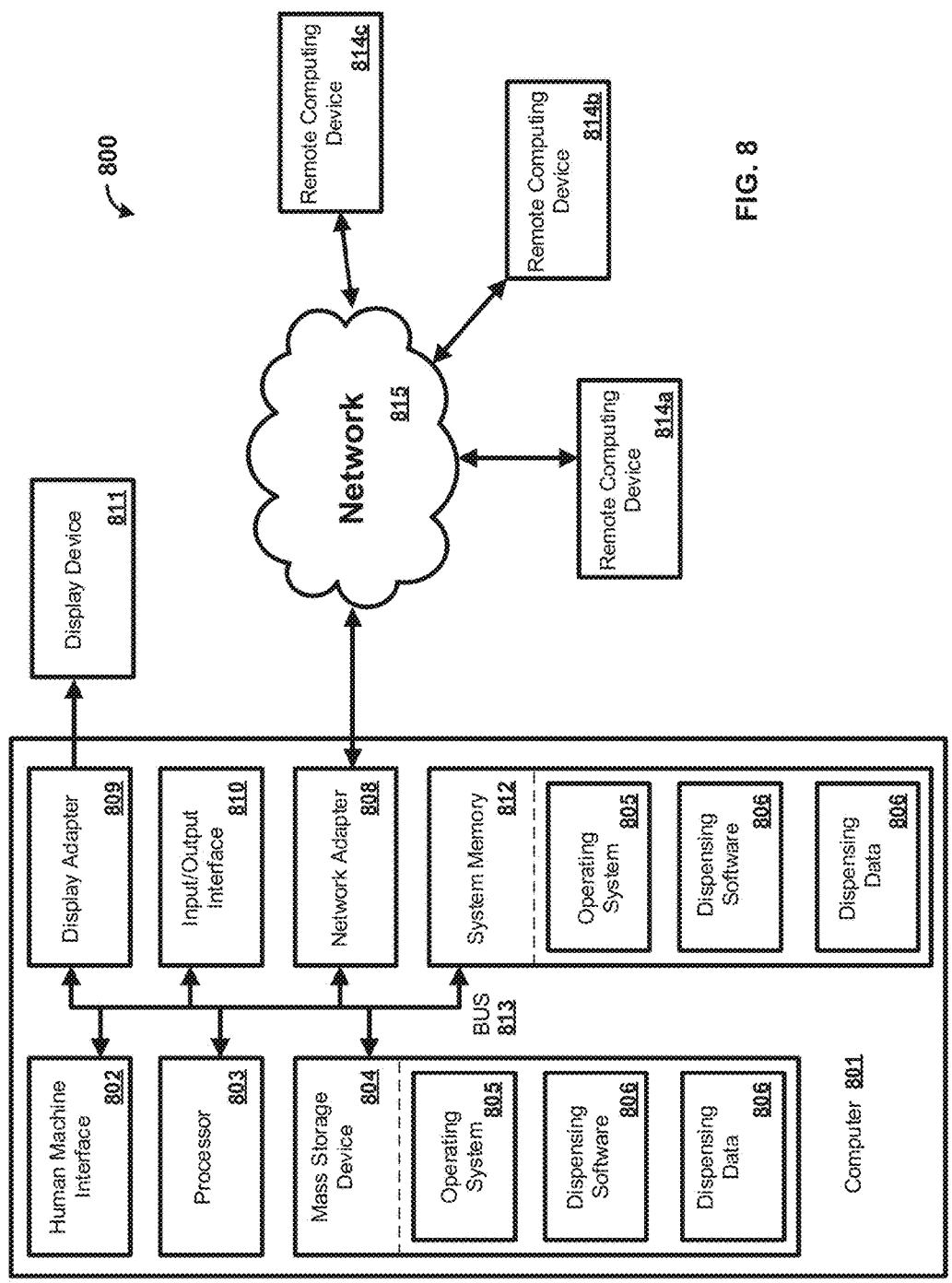
FIG. 8 is a block diagram illustrating an example computing device in which the present methods and systems can operate.

In an exemplary aspect, the methods and systems can be implemented on a computer 801 as illustrated in FIG. 8 and described below. By way of example, the holding device 102, the dispensing device 124, and the computing device 128 of FIG. 1 can be computers as illustrated in FIG. 8. Similarly, the methods and systems disclosed can utilize one or more computers to perform one or more functions in one or more locations. FIG. 8 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 801. The components of the computer 801 can comprise, but are not limited to, one or more processors 803, a system memory 812, and a system bus 813 that couples various system components including the one or more processors 803 to the system memory 812. The system can utilize parallel computing.

The system bus 813 represents one or more of several possible types of bus structures, including a memory bus or memory controller, a peripheral bus, an accelerated graphics port, or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCM-CIA), Universal Serial Bus (USB) and the like. The bus 813, and all buses specified in this description can also be implemented over a wired or wireless network connection and each of the subsystems, including the one or more processors 803, a mass storage device 804, an operating system 805, dispensing software 806, dispensing data 807, a network adapter 808, the system memory 812, an Input/Output Interface 810, a display adapter 809, a display device 811, and a human machine interface 802, can be contained within one or more remote computing devices 814a,b,c at physically separate locations, connected through buses of this form, in effect implementing a fully distributed system.

The computer 801 typically comprises a variety of computer readable media. Exemplary readable media can be any available media that is accessible by the computer 801 and comprises, for example and not meant to be limiting, both volatile and non-volatile media, removable and non-removable media. The system memory 812 comprises computer readable media in the form of volatile memory, such as random access memory (RAM), and/or non-volatile memory, such as read only memory (ROM). The system memory 812 typically contains data such as the dispensing data 807 and/or program modules such as the operating system 805 and the dispensing software 806 that are immediately accessible to and/or are presently operated on by the one or more processors 803.

In another aspect, the computer 801 can also comprise other removable/non-removable, volatile/non-volatile computer storage media. By way of example, FIG. 8 illustrates the mass storage device 804 which can provide non-volatile storage of computer code, computer readable instructions, data structures, program modules, and other data for the computer 801. For example and not meant to be limiting, the mass storage device 804 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 804, including by way of example, the operating system 805 and the dispensing software 806. Each of the operating system 805 and the dispensing software 806 (or some combination thereof) can comprise elements of the programming and the dispensing software 806. The dispensing data 807 can also be stored on the mass storage device 804. The dispensing data 807 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 801 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the one or more processors 803 via the human machine interface 802 that is coupled to the system bus 813, but can be connected by other interface and bus structures, such as a parallel port, game port, an IEEE 1394 Port (also known as a Firewire port), a serial port, or a universal serial bus (USB).

In yet another aspect, the display device 811 can also be connected to the system bus 813 via an interface, such as the display adapter 809. It is contemplated that the computer 801 can have more than one display adapter 809 and the computer 801 can have more than one display device 811. For example, the display device 811 can be a monitor, an LCD (Liquid Crystal Display), or a projector. In addition to the display device 811, other output peripheral devices can comprise components such as speakers (not shown) and a printer (not shown) which can be connected to the computer 801 via the Input/Output Interface 810. Any step and/or result of the methods can be output in any form to an output device. Such output can be any form of visual representation, including, but not limited to, textual, graphical, animation, audio, tactile, and the like. The display device 811 and computer 801 can be part of one device, or separate devices.

The computer 801 can operate in a networked environment using logical connections to one or more remote computing devices 814a,b,c. By way of example, a remote computing device can be a personal computer, portable computer, smartphone, a server, a router, a network computer, a peer device or other common network node, and so on. Logical connections between the computer 801 and a remote computing device 814a,b,c can be made via a network 815, such as a local area network (LAN) and/or a general wide area network (WAN). Such network connections can be through the network adapter 808. The network adapter 808 can be implemented in both wired and wireless environments. Such networking environments are conventional and commonplace in dwellings, offices, enterprise-wide computer networks, intranets, and the Internet.

For purposes of illustration, application programs and other executable program components such as the operating system 805 are illustrated herein as discrete blocks, although it is recognized that such programs and components reside at various times in different storage components of the computing device 801, and are executed by the one or more processors 803 of the computer. An implementation of the dispensing software 806 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning. Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A system for dispensing a calibrated amount of a monitored material, the system comprising a holding device, the holding device comprising:
   a holding device processor operable to control the holding device;
   a container configured to store a monitored liquid therein, wherein the container includes a transfer outlet for transferring at least a portion of the monitored liquid to an associated dispensing device;
   a sensing component operatively coupled to the holding device processor and controlled in part by the holding device processor, wherein the sensing component is configured to detect usage data associated with the monitored liquid stored in the container, and transmit the detected usage data to the holding device processor;
   an authentication input component operatively coupled to the holding device processor and controlled in part by the holding device processor, wherein the authentication input component is configured to receive a plurality of authentication data from an associated user and transmit the authentication data to holding device processor;
   a capping component positioned proximate to the transfer outlet of the container, wherein the capping component is configured to prevent monitored liquid from exiting the container prior to activation of the holding device to transfer at least a portion of the monitored liquid to the associated dispensing device, wherein the capping component is further configured to matingly engage with the associated dispensing device for transfer of at least a portion of the monitored liquid via the transfer outlet to the associated dispensing device;
   an actuation component operatively coupled to the holding device processor and controlled in part by the holding device processor, wherein the actuation component is operable to control activation of the capping component to transfer at least a portion of the monitored liquid to the associated dispensing device;
   wherein the holding device processor is further operable to:
      receive at least a portion of the detected usage data from the sensing component;
      determine, based on at least a portion of the detected usage data, at least one usage condition of the monitored liquid;
      receive at least a portion of the authentication data from the authentication input component;
      determine, based on at least a portion of the authentication input data, an authorization status of the associated user; and
      generate, based on at least one determined usage condition and authorization status of the associated user, at least one activation control signal for controlling the activation of the actuation component to transfer at least a portion of the monitored liquid to the associated dispensing device.

2. The system of claim 1, wherein the holding device further comprises a memory operatively coupled to the holding device processor, wherein the memory is operable to store a plurality of the generated usage data associated with the monitored liquid stored in the container.

3. The system of claim 1, wherein the sensing component is further operable to detect a plurality of status data associated with at least one operational characteristic of the holding device and transmit the detected status data to the holding device processor,
   wherein the holding device processor is further operable to:
      receive at least a portion of the detected status data from the sensing component;
      determine, based on at least a portion of the detected status data, at least one operational status of the holding device;
      generate, based on at least one determined operational status, at least one activation control signal for controlling the activation of the actuation component to transfer at least a portion of the monitored liquid to the associated dispensing device.

4. The system of claim 1, wherein the holding device further comprises a holding input/output device operatively coupled to the holding device processor and controlled in part by the holding device processor, wherein the input/output device is configured to transmit at least a portion of at least one of the plurality of usage data, the plurality of status data, and the plurality of authentication input data to a remote device for processing thereof.

5. The system of claim 4,
wherein the holding input/output device is further operable to receive at least one command from the remote device for controlling the activation of the actuation component to transfer at least a portion of the monitored liquid to the associated dispensing device and transmit the at least one command to the holding device processor;
wherein the holding device processor is further operable to receive the at least one command and generate, based on the at least one command, at least one activation control signal for controlling the activation of the actuation component to transfer at least a portion of the monitored liquid to the associated dispensing device.

6. The system of claim 5, wherein the at least one command for controlling the activation of the actuation component to transfer at least a portion of the monitored liquid to the associated dispensing device comprises at least one of controlling an amount of monitored liquid to be transferred to the associated dispensing device, controlling an authorization status of an associated user, controlling a frequency of a transfer of monitored liquid to the associated dispensing device, and combinations thereof.

7. The system of claim 1, further comprising a dispensing device, the dispensing device comprising:
a dispensing device processor operable to control the dispensing device;
a receptacle configured to receive a calibrated of monitored liquid transferred by the holding device; and
a dispensing unit configured to dispense the calibrated amount of monitored liquid to the associated user.

8. The system of claim 7, wherein the dispensing unit further comprises a pressure component operatively coupled to the dispensing device processor and controlled in part by the dispensing device processor; wherein the pressure component is configured to generate a negative pressure within the receptacle to cause at least a portion of the monitored liquid to be transferred from the holding device to the receptacle.

9. The system of claim 8, wherein the dispensing component comprises a hollow needle configured to inject the calibrated amount of monitored liquid into the associated user.

10. A system for dispensing a calibrated amount of a monitored liquid, the system comprising a holding device and a dispensing device,
the holding device comprising:
a holding device processor operable to control the holding device;
a container configured to store a monitored liquid therein, wherein the container includes a transfer outlet for transferring at least a portion of the monitored liquid to the dispensing device;
a sensing component operatively coupled to the holding device processor and controlled in part by the holding device processor, wherein the sensing component is configured to detect usage data associated with the monitored liquid stored in the container, and transmit the detected usage data to the holding device processor;
an authentication input component operatively coupled to the holding device processor and controlled in part by the holding device processor, wherein the authentication input component is configured to receive a plurality of authentication data from an associated user and transmit the authentication data to holding device processor;
a capping component positioned proximate to the transfer outlet of the container, wherein the capping component is configured to prevent monitored liquid from exiting the container prior to activation of the holding device to transfer at least a portion of the monitored liquid to the dispensing device, wherein the capping component is further configured to matingly engage with the dispensing device for transfer of at least a portion of the monitored liquid via the transfer outlet to the associated dispensing device;
an actuation component operatively coupled to the holding device processor and controlled in part by the holding device processor, wherein the actuation component is operable to control activation of the capping component to transfer at least a portion of the monitored liquid to the dispensing device;
wherein the holding device processor is further operable to:
receive at least a portion of the detected usage data from the sensing component;
determine, based on at least a portion of the detected usage data, at least one usage condition of the monitored liquid;
receive at least a portion of the authentication data from the authentication input component;
determine, based on at least a portion of the authentication input data, an authorization status of the associated user; and
generate, based on at least one determined usage condition and authorization status, at least one activation control signal for controlling the activation of the actuation component to transfer at least a portion of the monitored liquid to the dispensing device;
the dispensing device comprising:
a dispensing device processor operable to control the dispensing device;
a receptacle configured to receive a calibrated of monitored liquid transferred by the holding device; and
a dispensing unit configured to dispense the calibrated amount of monitored liquid to the associated user.

11. The system of claim 10, wherein the holding device further comprises a memory operatively coupled to the holding device processor, wherein the memory is operable to store a plurality of the generated usage data associated with the monitored liquid stored in the container.

12. The system of claim 10, wherein the sensing component is further operable to detect a plurality of status data associated with at least one operational characteristic of the holding device and transmit the detected status data to the holding device processor,
wherein the holding device processor is further operable to:
receive at least a portion of the detected status data from the sensing component;

determine, based on at least a portion of the detected status data, at least one operational status of the holding device;

generate, based on at least one determined operational status, at least one activation control signal for controlling the activation of the actuation component to transfer at least a portion of the monitored liquid to the dispensing device.

13. The system of claim 10, wherein the holding device further comprises a holding input/output device operatively coupled to the holding device processor and controlled in part by the holding device processor, wherein the input/output device is configured to transmit at least a portion of at least one of the plurality of usage data, the plurality of status data, and the plurality of authentication input data to a remote device for processing thereof.

14. The system of claim 13, wherein the holding input/output device is further operable to receive at least one command from the remote device for controlling the activation of the actuation component to transfer at least a portion of the monitored liquid to the dispensing device and transmit the at least one command to the holding device processor;

wherein the holding device processor is further operable to receive the at least one command and generate, based on the at least one command, at least one activation control signal for controlling the activation of the actuation component to transfer at least a portion of the monitored liquid to the dispensing device.

15. The system of claim 14, wherein the at least one command for controlling the activation of the actuation component to transfer at least a portion of the monitored liquid to the dispensing device comprises at least one of controlling an amount of monitored liquid to be transferred to the dispensing device, controlling an authorization status of an associated user, controlling a frequency of a transfer of monitored liquid to the dispensing device, and combinations thereof.

16. The system of claim 10, wherein the dispensing unit further comprises a pressure component operatively coupled to the dispensing device processor and controlled in part by the dispensing device processor; wherein the pressure component is configured to generate a negative pressure within the receptacle to cause at least a portion of the monitored liquid to be transferred from the holding device to the receptacle.

17. The system of claim 16, wherein the dispensing component comprises a hollow needle configured to inject the calibrated amount of monitored liquid into the associated user.

* * * * *